US008955721B2

(12) United States Patent
Dönmez

(10) Patent No.: US 8,955,721 B2
(45) Date of Patent: Feb. 17, 2015

(54) DEVICE FOR DISPENSING A DENTAL MATERIAL

(71) Applicant: 3M Innovative Properties Company, Saint Paul, MN (US)

(72) Inventor: Özcan Dönmez, Landsberg am Lech (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 14/353,970

(22) PCT Filed: Nov. 19, 2012

(86) PCT No.: PCT/US2012/065847
§ 371 (c)(1),
(2) Date: Apr. 24, 2014

(87) PCT Pub. No.: WO2013/078131
PCT Pub. Date: May 30, 2013

(65) Prior Publication Data
US 2014/0305968 A1 Oct. 16, 2014

(30) Foreign Application Priority Data
Nov. 21, 2011 (EP) .................................... 11190004

(51) Int. Cl.
*B05C 17/01* (2006.01)
*B05C 17/005* (2006.01)
(Continued)

(52) U.S. Cl.
CPC ......... *A61C 9/0026* (2013.01); *B05C 17/00553* (2013.01); *B05C 17/0103* (2013.01); *B65D 83/0011* (2013.01); *B05C 17/0133* (2013.01)
USPC .......... 222/390; 222/145.5; 222/94; 222/137; 74/424.78

(58) Field of Classification Search
CPC ............ B05C 17/0103; B05C 17/0133; B05C 17/00553; A61C 5/064; A61C 5/062; A61C 5/068
USPC .............. 222/145.6, 135, 136, 137, 333, 392, 222/390; 74/424.78; 604/191, 155; 433/90, 433/89
See application file for complete search history.

(56) References Cited

U.S. PATENT DOCUMENTS 1,328,567 A * 1/1920 Jones ............................ 222/390
2,865,241 A 12/1958 Farrow
(Continued)

FOREIGN PATENT DOCUMENTS

DE 10122961 11/2002
DE 102006037585 2/2008
(Continued)

OTHER PUBLICATIONS

Extended European Search Report for EP11190004 dated Apr. 3, 2012.
(Continued)

*Primary Examiner* — Paul R Durand
*Assistant Examiner* — Charles P Cheyney
(74) *Attorney, Agent, or Firm* — 3M Innovative Properties Company; Qiang Han

(57) ABSTRACT

A device (100) for dispensing a dental material which comprises a spindle drive (10) for driving a piston (111) for extruding the dental material. The spindle drive (10) comprises a pair of threaded spindles and a clasp nut member (20) which is adapted for engaging with anyone of the spindles. The clasp nut member has first and second thread structures (11, 12) which are offset relative to each other by about ½ of the pitch of the thread of the spindle or the thread structures (11, 12) in a dimension of the pitch.

15 Claims, 4 Drawing Sheets

110 115 20 10 11 116 A1 A A2 117 111 12 114 113 112

23 21 A 22 24 20 X B1 B2

(51) Int. Cl.
*A61C 9/00* (2006.01)
*B65D 83/00* (2006.01)

(56) References Cited

U.S. PATENT DOCUMENTS

| | | | | |
|---|---|---|---|---|
| 5,286,105 | A | 2/1994 | Herold | |
| 5,450,988 | A * | 9/1995 | Jerdee | 222/333 |
| 5,477,988 | A * | 12/1995 | Gerich | 222/137 |
| 5,538,778 | A | 7/1996 | Hurwitz | |
| 5,667,871 | A | 9/1997 | Goodrich | |
| 5,782,735 | A | 7/1998 | Goodrich | |
| 6,168,052 | B1 | 1/2001 | Keller | |
| 6,854,621 | B2 * | 2/2005 | Keller | 222/137 |
| 8,800,402 | B2 * | 8/2014 | Weum | 74/424.79 |
| 2010/0128559 | A1 | 5/2010 | Keller | |
| 2012/0148980 | A1 * | 6/2012 | Gramann | 433/90 |

FOREIGN PATENT DOCUMENTS

| | | |
|---|---|---|
| EP | 1700639 | 9/2006 |
| EP | 2324792 | 5/2011 |

OTHER PUBLICATIONS

International Search Report for PCT/US2012/265847 mailed Apr. 29, 2013.

* cited by examiner

DEVICE FOR DISPENSING A DENTAL MATERIAL

CROSS REFERENCE TO RELATED APPLICATIONS

This application is a national stage filing under 35 U.S.C. 371 of PCT/US2012/065847, filed Nov. 19, 2012, which claims priority to European Application No. 11190004.9, filed Nov. 21, 2011, the disclosures of which are incorporated by reference in their entirety herein.

FIELD OF THE INVENTION

The invention relates to a device for dispensing a dental material, which comprises a spindle drive for driving a piston for extruding the dental material. In particular the invention relates to the spindle drive which comprises a pair of threaded spindles and a clasp nut member for engaging with the spindles.

BACKGROUND ART

In dentistry a variety of devices are available which allow for preparation and/or application of dental materials in a dentist's practice. In particular for preparation of materials that are typically used at larger amounts, like for example dental impression materials, devices have been developed that provide for automatic dispensing from packages and/or for mixing of such materials. An exemplary device for mixing and dispensing a dental impression material is for example available under the designation 3M™ ESPE™ Pentamix™ from 3M ESPE AG, Germany. Typically such a device allows for two material components to be simultaneously supplied from a package through a mixer where they are mixed. Often the devices provide for continuously extruding the components through a mixer, where the components are mixed as the components flow through the mixer and released from an outlet.

The devices further typically have a motor driven piston for extruding the material from a container. A variety of different drive concepts have been proposed for driving the piston at a relatively high force as it may be required for appropriately dispensing the dental material.

For example EP 1 700 639 discloses a device for dispensing a flowable substance. The device comprises at least one force transmitting member (for example a push-pull chain) adapted to transmit a pushing force in a direction toward or opposite the substance and which can be gathered non-linearly.

U.S. Pat. No. 6,168,052 discloses an electrically driven dispensing appliance having an electric drive which acts via drive screws on thrust plates for dispensing material from cartridges. The drive screws are axially stationary and are in action relationship with a slide bearing said thrust plates. The electric drive comprises a first gear motor for a drive under high load during advance and relief, and a second motor for the drive under lower load during the retracting and fast advance motions.

Although there are a variety of devices on the market which provide for automatic mixing and dispensing there is still a desire to minimize costs for manufacturing of such devices and for providing the devices with maximized reliability.

SUMMARY

The invention relates to a device for dispensing a dental material. The device comprises a spindle drive for driving at least one piston for extruding the dental material from a container. The spindle drive comprises a pair of threaded spindles which extend generally parallel to a longitudinal axis. The spindles are further preferably arranged generally parallel to each other, and preferably side by side. The threads of the spindles base on the same pitch. The spindle drive comprises further a clasp nut member which has a first thread structure and a second thread structure. Each of the first and second thread structures being adapted for engaging with the thread of anyone of the spindles to establish a screw connection between the clasp nut member and the spindles. The first and second thread structures are offset relative to each other by about ½ of the pitch, or multiple pitches less or minus about ½ of the pitch, in a direction oriented parallel to the longitudinal axis.

The term "pitch" for the purpose of this specification is understood as the pitch of a screw or spindle thread, preferably of a single start thread. The pitch may for example be measured from the distance between two directly neighboring crests of the thread in a dimension of a linear center axis along which the thread extends. The pitch of a trapezoid thread may alternatively be measured from the distance between two directly neighboring flanks facing in the same direction. Therefore the pitch is also defined by a distance which extends along a dimension parallel to the center axis of the thread.

Accordingly the first and second thread structures are offset relative to each other by about ½ of the pitch, or multiple pitches less or minus about ½ of the pitch, in a dimension of the pitch.

The invention may be advantageous in that it allows a relatively simple and compact design of the device. In particular complex gear boxes may not be required. A design which is enabled by the invention may further help minimizing the amount of differently designed parts within the device. This further may allow for minimizing the amount of tools required for manufacturing the device, for example two cooperating injection molded clasp nut members may be molded using the same mold. Further a relatively robust device may be obtained by use of the invention. The invention may further be advantageous in that it may enable relatively slow or extremely slow extrusion speeds of the material. This may allow the dispensation of relatively high viscous materials for example. The invention may further allow the use of relatively small and/or inexpensive motors.

In one embodiment the first and second thread structures correspond in shape to two different portions of one common imaginary thread shape. The common thread shape may have an imaginary center axis around which the imaginary thread extends and the two different portions are preferably offset relative to each other by about 180 degrees about the center axis. In other words the first thread structure may correspond in shape to a half section of the common imaginary thread shape along the center axis and the second thread structure may correspond in shape to the other half section of the common imaginary thread shape along the center axis. The two different portions are preferably also offset relative to each other by about ½ of the pitch of the common thread in a dimension parallel to the thread axis.

In one embodiment the thread of each the spindles corresponds to an outer trapezoid thread. Each of the first and second thread structures may correspond to partial inner trapezoid threads which are adapted, in particular sized and shaped, to form a screw connection with anyone of the outer spindle threads. The skilled person will be aware that instead of partial inner threads other structures may be used which allow for forming a screw connection with the outer spindle threads.

In a further embodiment the spindles are rotationally coupled such that a rotation of one spindle causes also the other spindle to rotate. Preferably the spindles are rotationally coupled such that they are restricted to rotate at the same speed and in the same direction of rotation. Therefore each of the spindles may be coupled by at least three gears, with two non-engaging spindle gears being fixed on the respective spindles and another intermediate gear coupling the two gears. The skilled person will however recognize other couplings providing a similar or equivalent solution.

In one embodiment the clasp nut member is adapted for disengageable engagement with the spindles. In particular the clasp nut member, for engaging and disengaging the spindles, is movably arranged relative to the spindles in a dimension laterally to the longitudinal axis. Therefore the clasp nut member is preferably movable between an engaged position and a disengaged position. Preferably in the engaged position the first thread structure of the clasp nut member and the thread of one of the spindles are engaged, and the second thread structure of the clasp nut member and the thread of the other one of the spindles are engaged. Further preferably in the disengaged position the first thread structure of the clasp nut member and the thread of one of the spindles are disengaged, and the second thread structure of the clasp nut member and the thread of the other one of the spindles are disengaged. Preferably the clasp nut member can be moved between the engaged position and the disengaged position by moving the clasp nut toward or away from the spindles, respectively.

In one embodiment the clasp nut member has at least two generally semicircular grooves each accommodating one of the first and second thread structures. The grooves are preferably arranged side by side and generally parallel to each other.

In a further embodiment the thread structures comprise at least one helical ridge extending about 180 degrees or less than 180 degrees around a thread axis that is arranged parallel to the longitudinal axis. The helical ridge may further extend less than 180 degrees, for example between 30 degrees and 150 degrees about thread axis. Each of the first and second thread structures may comprises at least four ridges which together form a partial inner thread. It has however been found that one, two, or three ridges may generally form equivalent alternatives to four ridges depending on the forces required to dispense the dental material or depending on the material used for the ridges and/or the first and second thread structures.

In one embodiment the clasp nut member is adapted to directly or indirectly move the piston. For example the device may have a carrier for the clasp nut, and that carrier may be connected to the piston. In particular the piston may be part of the carrier or mounted to the carrier, for example the clasp nut member may be connected to a carrier which carries the piston.

In a further embodiment the clasp nut member may have two pistons. At least one or both of the pistons may form a blind hole into which the respective spindle may be receivable as the carrier and the spindles move relative to each other. Accordingly the spindles may be prevented from getting in contact with the material pressurized by the pistons and eventually flowing behind fronts of the pistons.

In one embodiment the carrier and the clasp nut member are adapted to cooperate such that a movement of the clasp nut member relative to the spindle in a dimension parallel to the longitudinal axis also causes the carrier to be moved relative to the spindles in the same dimension parallel to the longitudinal axis. On the other hand the carrier and the clasp nut member may be adapted such that the clasp nut member is movable relative to the spindles in a dimension laterally to the spindles independent from the carrier. In one example the carrier and the clasp nut member are adapted such that the clasp nut member is enabled for a movement relative to the carrier in a dimension laterally to the spindles but blocked for a movement relative to the carrier in a dimension parallel to the spindles.

In one embodiment the clasp nut member is made of a polymer. The clasp nut member may in particular be made of a thermoplastic polymer. The polymer may be selected from among polyoxymethylene, polyamide, acrylonitrile-butadiene-styrene terpolymer, polybutadiene terephthalate, polycarbonate, and polytetrafluoroethylene. The polymer may further comprise carbon or glass fibers. Further the clasp nut member may be made of two or more combinations of different materials, for example a plastic or polymer material which comprise first and second thread structures made of metal, for example metal ridges. The clasp nut member may for example be injection molded. The spindles may be made of steel, for example a stainless steel.

In a further embodiment the device has a further clasp nut member. The clasp nut members are preferably arranged for a movement from opposing sides relative to the spindles. In particular the clasp nut members are preferably arranged for a movement toward or away from each other in a dimension laterally to the longitudinal axis and with the spindles between the clasp nut members.

In one embodiment the device is adapted to retain the clasp nut members toward the engaged position. For example the clasp nut members may be urged toward the engaged position by spring force. This may allow for the clasp nut members to automatically move toward the disengaged position upon overload of the spindle drive, for example in case the force between the clasp nut member and the spindle become high enough to cause any of the spindle or the clasp nut members to damage. The device may further be adapted to lock the clasp nut members in the engaged position.

In a further embodiment the device is adapted such that the clasp nut members can be brought in the disengaged position to enable a movement of the piston independent from the spindles, for example independent from any rotation of the spindles. The device may be further adapted such that the clasp nut members can be brought in the engaged position to enable a movement of the piston by the spindles, for example by rotation of the spindles and thus causing the clasp nut members to move. A movement of the piston independent from the spindles may for example allow for the piston to be rapidly moved to any desired position. For example the piston may be quickly movable outside an empty container and repositioned toward a new container replacing the empty container.

In a further embodiment the clasp nut members have a guiding structure for guiding each another. Each of the clasp nut members may have a first guiding structure and a second guiding structure, wherein the shape of the first guiding structure corresponds generally to a negative shape of the second guiding structure. In one example each of the clasp nut members has a male guiding structure and a female guiding structure. In cooperation of the clasp nut members the male guiding structure of one clasp nut member may be mated with the female guiding structure of the other clasp nut member, and the female guiding structure of the one clasp nut member may be mated with the male guiding structure of the other clasp nut member. The male guiding structure may be a pin and the female guiding structure a corresponding hole. The clasp nut members may further by guided within the carrier.

In one embodiment the clasp nut members are of generally equal shape. In particular the clasp nut members may be made based on the same design. Accordingly the clasp nut members may differ basically by manufacturing tolerances, but may otherwise be identical. Thus only one clasp nut member design or one type of clasp nut member may be used for the device. This may be advantageous in that this helps minimizing the amount of different parts in the device. This may further help minimizing the manufacturing costs and costs for storage of parts. Further this may help maximizing the reliability in the assembly process because the clasp nut members cannot be mistaken.

In a preferred embodiment the device has a drive shaft for receiving and driving a mixer for mixing the components urged toward the dispensing area. The drive shaft may for example be driven by the intermediate gear coupling the spindle gears. Accordingly the device may be adapted for operating with a dynamic mixer. The device may further comprise two containers containing components of the dental material. Further the device may have a dynamic mixer for mixing the components. The device preferably has for each container a piston for extruding the respective component from the container toward the mixer. The device may have a motor for driving the spindle drive for driving the piston.

DETAILED DESCRIPTION OF THE INVENTION

Figure 1:
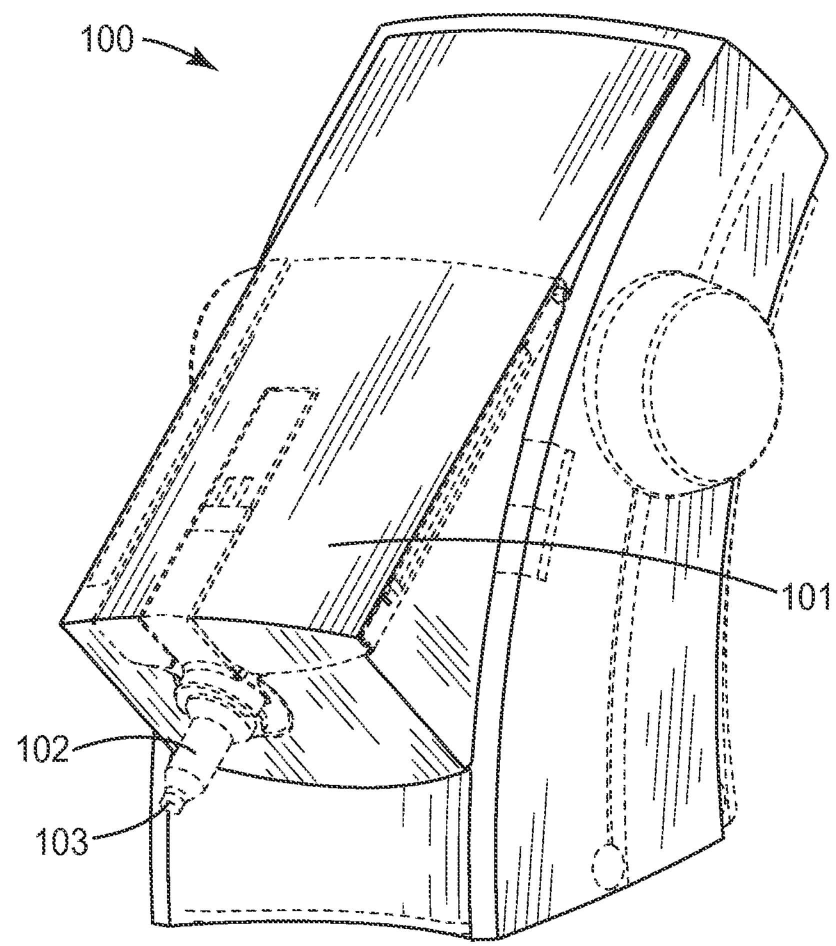
FIG. 1 is a perspective view of a device according to an embodiment of the invention.

FIG. 1 shows a device 100 for dispensing dental materials. The device 100 is adapted for receiving the material, preferably in the form of two separate components, in a receptacle (not visible in this view) of the device 100. The device 100 has further attached thereto a mixer 102 for mixing the components. The material components are preferably contained in separate containers (not shown) from which the components can be extruded into the mixer 102. The mixer 102 is connected with the containers such that the individual components can be advanced into a mixing chamber of the mixer where the components can be mixed, for example by help of a rotating mixing rotor which causes the components to merge to form a mixture. The mixture can exit through an outlet 103 of the mixer 120. The device 100 shown may be used to mix and dispense a hardenable dental impression material, for example. Mixed dental impression material may for example be used to fill a dental tray which is then placed into a patient's mouth for taking a dental impression. The mixer 102 of the device 100 shown is replaceably attached at the device 100. Therefore when the mixed material hardens and thus blocks the mixer the used mixer may be replaced by an unused mixer for the next use of the device 100. A similar device is available under the designation 3M™ ESPE™ Pentamix™ from 3M ESPE AG, Germany.

Figure 2:
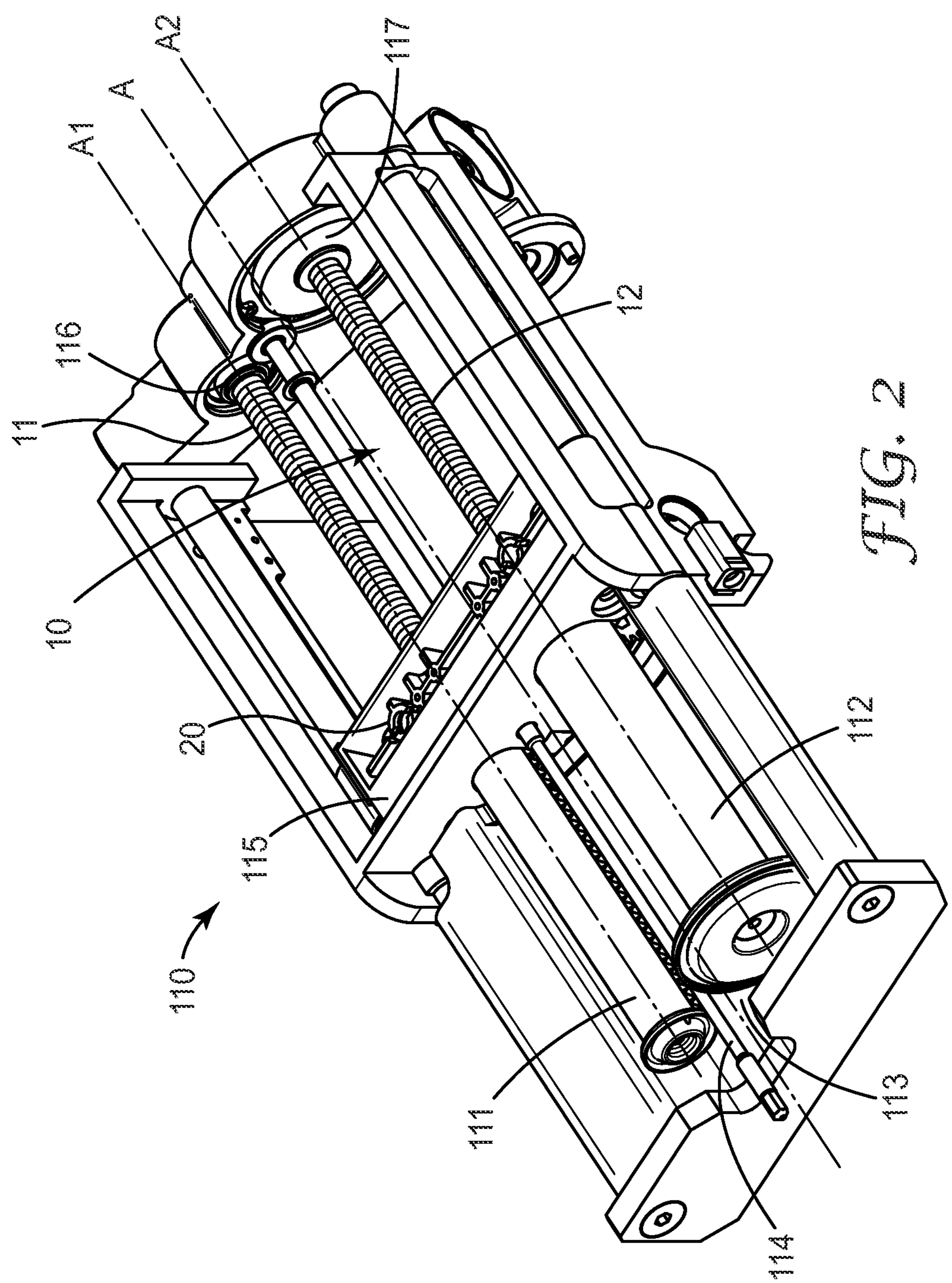
FIG. 2 is a perspective view of an assembly with a spindle drive according to an embodiment of the invention.

FIG. 2 shows a drive assembly 110 as it may be incorporated in the dispensing device shown in FIG. 1. In the example the drive assembly 110 has a first piston 111 and a second piston 112 which are moveable within the receptacle 113. The receptacle 113 is configured for receiving a container or two separate containers (neither being shown in this view) which contain the dental material or components thereof. By moving the first and second pistons 111, 112 the dental material or components can be extruded from the container(s). The drive assembly 110 in the example additionally has a rotatable drive shaft 114 for driving the mixing rotor of a mixer (not shown in this view).

The drive assembly 110 further comprises a spindle drive 10 for driving the first and second pistons 111, 112. The spindle drive 10 has a first threaded spindle 11 and a second threaded spindle 12. The first and second threaded spindles 11, 12 are arranged side by side and generally parallel to each other. Further the first and second spindles 11, 12 have first and second spindle axes A1, A2, respectively, which may correspond to rotation axes or center axes of the respective spindles. In particular the first and second spindles 11, 12 are arranged with their spindle axes A1, A2 generally parallel to each other, and further generally parallel to a longitudinal axis A. The first and second spindles 11, 12 are based on the same thread diameter and the same pitch. In the example the first and second spindles 11, 12 are generally identical (meaning being made in accordance with the same design, but may slightly differ due to manufacturing tolerances). The spindle drive 10 further has a clasp nut member 20 which is adapted for engaging the first and second spindles 11, 12. In particular the clasp nut member 20 has a first thread structure (not visible) which in the illustrated example engages the thread of the first spindle 11 and a second thread structure (not visible) which in the illustrated example engages the thread of the second spindle 12. Thus upon rotation of the first and second spindles 11, 12 the clasp nut member 20 moves linearly relative to the spindles in a dimension parallel to the longitudinal axis A. That linear movement may be used for moving the first and second pistons 111, 112, for example in the same dimension parallel to the longitudinal axis A. In the example the first and second pistons 111, 112 are fixed at a carrier 115 which bears the clasp nut member 20. The carrier 115 and the clasp nut member 20 are adapted such that the clasp nut member 20 can entrain or drive the carrier 115 (and thus the pistons 111, 112) in a movement of the clasp nut member 20 in the dimension parallel to the longitudinal axis A. In particular the carrier 115 and the clasp nut member 20 are coupled with one another in only the dimension parallel to the longitudinal axis, which is also preferably the dimension in which the pistons are moved for extruding the dental material or the components thereof. The clasp nut member 20 is however preferably movable relative to the carrier 115 in a dimension laterally to the longitudinal axis A (or laterally to the spindle axes A1, A2). Thus the clasp nut member 20 is preferably also movable away and toward the first and second spindles 11, 12 in the dimension laterally to the longitudinal axis A. Accordingly the clasp nut member 20 is movable toward the spindles 11, 12 into an engaged position, in which the clasp nut member 20 engages with the spindles 11, 12, and away from the spindles 11, 12 into a disengaged position, in which the clasp nut member 20 is disengaged from the spindles 11, 12. Thus the clasp nut member 20 is adapted for disengageable engagement with the spindles 11, 12. Thereby the carrier 115 may be selectively coupled with or decoupled from the spindles 11, 12 of the spindle drive 10. This preferably allows for the pistons 111, 112 to be selectively driven by use of the spindles 11, 12 or moved independently from the spindles 11, 12. In the engaged position of the clasp nut member 20 and the spindles 11, 12 the spindle drive 10 preferably allows for driving the pistons 111, 112 at relatively high forces, but relatively low speed. Further in the disengaged position of the clasp nut member 20 and the spindles 11, 12 the spindle drive 10 may allow for rapidly moving the pistons 111, 112 at relatively low forces, for example may enable a rapid manual movement of the pistons 111, 112. Such a rapid movement may be advantageous for removing the pistons 111, 112 from a used dental material container to replacing that container by another container, for example.

The carrier 115 preferably guides the clasp nut member 20 in the dimension laterally to the longitudinal axis A. Therefore the carrier may comprise or form a guide for the clasp nut member 20. This guide may restrict a movement of the clasp nut member 20 and the carrier 115 relative to each other in the dimension parallel to the longitudinal axis A, but enable a movement of the clasp nut member 20 and the carrier 115 relative to each other in the dimension laterally (or perpendicularly) to the longitudinal axis A.

The drive assembly 110 of the example has first and second gears 116, 117 for driving the first and second spindles 11, 12, respectively. Although not shown in detail the gears 116, 117 are preferably connected—optionally via further gears—to a motor (not shown) for driving the gears. The skilled person will recognize several ways of driving the spindles, like for example by use of a gear box, a worm drive, and a belt or tooth belt. Any transmission which provides the spindles to be synchronously driven may be used for coupling the spindles and a motor or motors. Further the spindles may be driven directly or via a transmission by individual motors which are mechanically and/or electronically synchronized.

The skilled person will recognize that the components illustrated in FIG. 2 may not necessarily be combined in a common assembly as shown, but may be directly mounted in the dispensing device (for example in the housing of the dispensing device) as individual components. However such an assembly has been proven to be advantageous for minimizing assembly efforts and for maximizing the mechanical stability of the device independent from the design and stability of the housing. This further helps maximizing freedom in the design of the housing.

Figure 3:
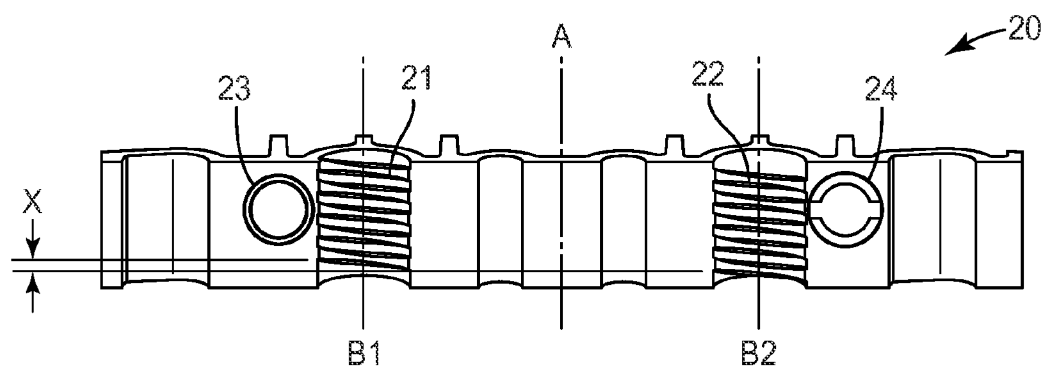
FIG. 3 is a perspective view of a clasp nut member according to an embodiment of the invention.

FIG. 3 shows the clasp nut member 20 in more detail. The clasp nut member 20 has a first thread structure 21 and a second thread structure 22. Each of the first and second thread structures 21, 22 are adapted for engaging with the thread of any of the spindles (not shown in this view) of the spindle drive shown in FIG. 2. In the example the thread structures 21, 22 correspond to half segments of an inner thread. The half segments of the inner thread are formed in side by side generally parallel grooves in the clasp nut member 20. The skilled person will recognize that instead of the thread structures illustrated other structures capable of engaging with a spindle thread may be used. For example a pin or other protrusion, optionally without any groove in the clasp nut member, may be used. Further the skilled person will recognize that instead of a half segment a smaller segment of a thread may be used.

The first and second thread structures 21, 22 have associated thread axes B1, B2 respectively. Each thread axis preferably generally corresponds to an axis along which a spindle axis extends in the engaged position of the clasp nut member 20 and corresponding spindles. In the example shown the thread axes B1, B2 correspond to center axes of the thread segments. However in case a pin or other protrusion is used instead of a thread segment a thread axis may generally correspond to the spindle axis of a spindle with which the pin or protrusion engages. Generally the thread axes B1, B2 are generally parallel to each other. Further the thread axes B1, B2 are generally parallel to the longitudinal axis A of a spindle drive (as shown in FIG. 2) with which the clasp nut member 20 may be used.

The thread structures 21, 22 in the example are of generally identical shape, but are offset relative to each other in a dimension parallel to the longitudinal axis A. The offset in the example is indicated by the distance X and corresponds to about ½ of the pitch of the thread structures. The pitch of the thread structures preferably corresponds to the pitch of spindles with which the clasp nut member 20 may be used. For example the pitch of the thread structures may correspond to the distance of two thread ridges of the thread structures 21, 22 or of the thread of a corresponding spindle.

Figure 4:
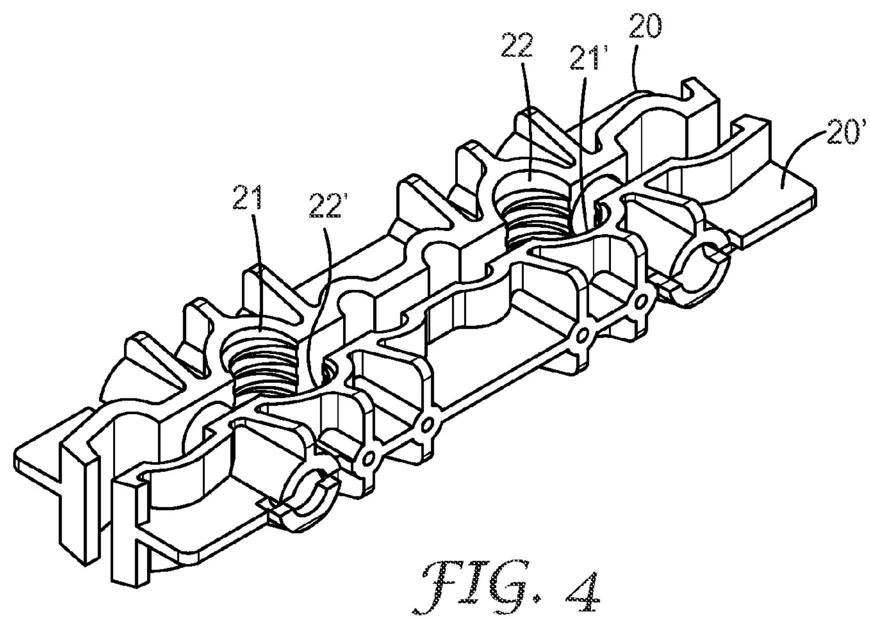
FIG. 4 is a perspective view of two cooperating clasp nut members according to an embodiment of the invention.

The clasp nut member 20 further has a first guiding structure 23 and a second guiding structure 24 for guiding with a further clasp nut member as described in FIG. 4.

FIG. 4 shows two generally identical clasp nut members 20, 20' in cooperation with each other. Each of the clasp nut members 20, 20' has a first guiding structure 23/23' and a second guiding structure 24/24'. The first and second guiding structures 23/23', 24/24' are of complementary shape. Thus the first guiding structure 23 of the clasp nut member 20 and the second guiding structure 24' of the clasp nut member 20' can be mated with each other, and the second guiding structure 24 of the clasp nut member 20 and the first guiding structure 23' of the clasp nut member 20' can be mated with each other.

Further the first thread structure 21 of the clasp nut member 20 is located opposite to the second thread structure 22' of the clasp nut member 20', and the second thread structure 22 of the clasp nut member 20 is located opposite to the first thread structure 21' of the clasp nut member 20'. Thus in the example the half section of the thread of the first thread structure 21 of the clasp nut member 20 and the half section of the thread of the second thread structure 22' of the clasp nut member 20' in combination complement to a full inner thread. In other words the first thread structure forms a half of an inner thread and the second thread forms the missing other half of an inner thread so that the first thread of one clasp nut member together with the second thread structure of the other clasp nut member forms a full inner thread. This is enabled by the offset of the thread structures by ½ of the pitch or multiple pitches less or minus about ½ of the pitch.

Figure 5:
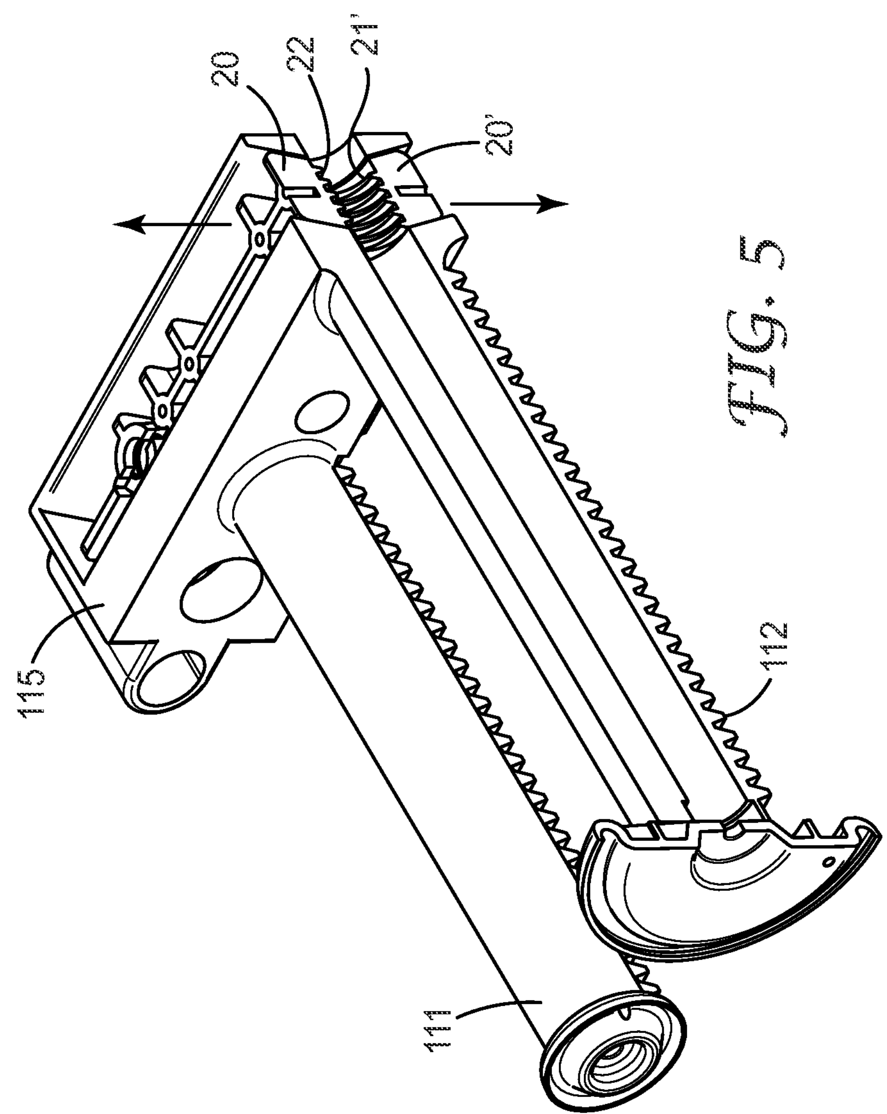
FIG. 5 is a perspective cross-sectional view of a carrier and two clasp nut members according to an embodiment of the invention.

FIG. 5 shows a cross-sectional view of the two cooperating clasp nut members 20, 20' within the carrier 115. The pair of clasp nut members 20, 20' is accommodated in the carrier 115 for driving the carrier 115, although a single clasp nut member 20/20' may be used in the alternative. Such a pair of clasp nut members 20, 20' preferably allows for driving the pistons 111, 112 for extruding dental material at higher forces than a single clasp nut member of the same design. Further an engagement of spindles (not shown) by two clasp nuts from opposite sides of the spindles preferably minimizes forces in a dimension laterally of the spindle axis in a situation where the clasp nut members are urged axially to the spindles. Due to the identical or generally identical design of the clasp nut members manufacturing and maintenance costs may be minimized.

As shown the first thread structure 21' and the second thread structure 22 complement to an inner thread which can engage with the thread of a spindle (not shown) to form a screw connection with the spindle. Due to the offset of the thread structures by ½ of the pitch the ends of thread ridges of one thread structure align with the ends of thread ridges of the other thread structure when the thread structures are arranged opposite to each other. In other words the thread ridges of one thread structure and the thread ridges of the other thread structure complement to a helical ridge.

As indicated by the arrows the clasp nut members may be moved away from or towards each other to open or close the inner thread, respectively and to disengage from or engage with the spindle, respectively. Therefore each of the clasp nut members is movable between an engaged position, in which the clasp nut member engages with the spindle, and a disengaged position, in which the clasp nut member is disengaged from the spindle.

The invention claimed is:

1. A device for dispensing a dental material, comprising: a spindle drive for driving at least one piston for extruding the dental material from a container, the spindle drive comprising:

a pair of threaded spindles extending generally parallel to a longitudinal axis, wherein the threads of the spindles base on the same pitch; and a clasp nut member having a first thread structure and a second thread structure, each of the first and second thread structures being adapted for engaging with the thread of anyone of the spindles to establish a screw connection between the clasp nut member and the spindles;

wherein the first and second thread structures are offset relative to each other by about ½ of the pitch in a direction oriented parallel to the longitudinal axis.

2. The device of claim 1, wherein the clasp nut member is adapted for disengageable engagement with the spindles.

3. The device of claim 2, wherein the clasp nut member, for engaging and disengaging the spindles, is movably arranged relative to the spindles in a dimension laterally to the longitudinal axis.

4. The device of claim 1, wherein the clasp nut member has at least two generally semicircular grooves each accommodating one of the first and second thread structures.

5. The device of claim 1, wherein each of the first and second thread structures comprises at least one helical ridge extending about 180 degrees or less than 180 degrees around a thread axis that is arranged parallel to the longitudinal axis.

6. The device of claim 5, wherein each of the first and second thread structures comprises at least four ridges together forming a partial inner thread.

7. The device of claim 1, wherein the clasp nut member is adapted to directly or indirectly move the piston.

8. The device of claim 7, wherein the clasp nut member is connected to a carrier which carries the piston.

9. The device of claim 1, wherein the clasp nut member is made of a polymer.

10. The device of claim 3, having a further clasp nut member, wherein the clasp nut members are arranged for a movement from opposing sides relative to the spindles.

11. The device of claim 10, wherein the clasp nut members have a guiding structure for guiding each another.

12. The device of claim 11, wherein each of the clasp nut members has a first guiding structure and a second guiding structure, wherein the shape of the first guiding structure corresponds generally to a negative shape of the second guiding structure.

13. The device of claim 9, wherein the clasp nut members are of generally equal shape.

14. The device of claim 1, further having a drive shaft for receiving and driving a mixer for mixing the components urged toward the dispensing area.

15. The device of claim 1, further comprising two containers containing components of the dental material, a dynamic mixer for mixing the components, for each container a piston for extruding the respective component from the container toward the mixer, and a motor for driving the spindle drive for driving the piston.

* * * * *